(12) United States Patent
Artal Soriano et al.

(10) Patent No.: US 10,898,073 B2
(45) Date of Patent: Jan. 26, 2021

(54) OPTOELECTRONIC BINOCULAR INSTRUMENT FOR THE CORRECTION OF PRESBYOPIA AND METHOD FOR THE BINOCULAR CORRECTION OF PRESBYOPIA

(71) Applicant: UNIVERSIDAD DE MURCIA, Murcia (ES)

(72) Inventors: Pablo Artal Soriano, Murcia (ES); Juan Mompean Esteba, Murcia (ES); Juan Luis Aragón, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 129 days.

(21) Appl. No.: 16/325,001

(22) PCT Filed: Jun. 16, 2017

(86) PCT No.: PCT/ES2017/070441
§ 371 (c)(1),
(2) Date: Feb. 12, 2019

(87) PCT Pub. No.: WO2018/029389
PCT Pub. Date: Feb. 15, 2018

(65) Prior Publication Data
US 2019/0175014 A1 Jun. 13, 2019

(30) Foreign Application Priority Data
Aug. 12, 2016 (ES) .................................. 201631094

(51) Int. Cl.
*A61B 3/11* (2006.01)
*A61B 3/00* (2006.01)
*G02C 7/08* (2006.01)

(52) U.S. Cl.
CPC ............ *A61B 3/111* (2013.01); *A61B 3/0008* (2013.01); *A61B 3/11* (2013.01); *A61B 3/112* (2013.01); *G02C 7/08* (2013.01)

(58) Field of Classification Search
CPC ......... A61B 3/111; A61B 3/0008; A61B 3/11; A61B 3/112; G02C 7/08
(Continued)

(56) References Cited

U.S. PATENT DOCUMENTS 8,911,084 B2 * 12/2014 Fernandez Martinez .................... A61B 3/1015 351/201
2008/0198330 A1 * 8/2008 Taylor .................. A61B 3/0091 351/209

(Continued)

*Primary Examiner* — James R Greece
(74) *Attorney, Agent, or Firm* — Ladas & Parry LLP

(57) ABSTRACT

Optoelectronic binocular instrument for the automatic correction of presbyopia and method for the binocular correction of the presbyopia. The instrument has two optoelectronic lenses (103, 110; 203, 204) and a capturing subsystem for taking images of the eye. By means of the pupil tracking, which performs the processing of the eye's images, the system determines the distance where the subject is looking at. The pupil tracking works at a very high speed, using a high-performance graphic processor and a highly parallelized algorithm for pupil tracking. The method consists of two phases. In the first one a calibration is accomplished, the subject is asked to look at targets at different distances and the size and position of the pupil is measured. In the second phase the correction is performed by the instrument, the system continuously captures and processes images to calculate the correction to apply and, finally, corrects the presbyopia by applying said correction.

6 Claims, 7 Drawing Sheets

(58) Field of Classification Search
USPC .......................................... 351/205–206, 246
See application file for complete search history.

(56) References Cited

U.S. PATENT DOCUMENTS

| | | | | |
|---|---|---|---|---|
| 2011/0299034 A1* | 12/2011 | Walsh | .................. | A61B 3/0091 351/206 |
| 2012/0038884 A1* | 2/2012 | Fernandez Martinez | ................... | A61B 3/14 351/201 |
| 2012/0154742 A1* | 6/2012 | Fernandez Martinez | ................... | A61B 3/1015 351/201 |

* cited by examiner

OPTOELECTRONIC BINOCULAR INSTRUMENT FOR THE CORRECTION OF PRESBYOPIA AND METHOD FOR THE BINOCULAR CORRECTION OF PRESBYOPIA

RELATED APPLICATION

This application is a national phase entry under 35 USC 371 of International Patent Application No.: PCT/ES2017/070441 filed on 16 Jun. 2017, which claims priority from Spanish Application No.: P201631094 filed on 12 Aug. 2016 the entire contents of which are incorporated herein by reference.

FIELD OF THE INVENTION

The current invention refers to an optoelectronic binocular instrument for the automatic correction of the presbyopia in the eye in real time and without the intervention of the subject, and to a method for the binocular correction of the presbyopia that uses such instrument.

BACKGROUND

Presbyopia affects 100% of the population older than 50 years. It is a natural process related to aging, which results in the eye's losing is capability to accommodate as it gets older. Therefore, the automatic presbyopia correction is a worldwide hot topic with a huge potential market.

Being such a big problem, some solutions have been proposed. However, most used solutions until now are partial and based on a static approach. Today's simplest solution is the utilization of monofocal glasses to look at near targets. Usually, these spectacles have a moderated correction that allow focusing near targets, however, defocusing far targets. Another solution which provides near and far focus vision with the same spectacles are the bifocal or progressive glasses. However, these lenses also have some problems regarding stereo vision and the training required to use the most appropriate area of the lens to look at each distance.

Another method widely used is known as monovision. This technique uses different focal points for each eye, one of them is always focusing at far while the other is always focusing at near. The brain selects the proper image depending on the distance where the person is looking at. However, this approach has big disadvantages. There is only a reduced range of distances which are perfectly in focus for each one of the eyes. Furthermore, the summation of the images of both eyes is impossible and, therefore, the stereo vision is affected as well.

There are some other systems based on using optoelectronic lenses like the one described in document US20120133891A1, where the optoelectronic lenses are proposed to correct myopia (not presbyopia) using a modified CMOS sensor to perform the tracking of the reflection of the cornea.

In document U.S. Pat. No. 8,690,321B2 the optoelectronic lenses are used to correct the presbyopia using an external camera which is used to perform the tracking of the face and the eyes of the subject. Later, the obtained information is sent to the spectacles. This invention is very limited since it depends on an external camera to the system to work.

In document WO2014179857A1 a system with adjustable lenses is proposed. This method uses the gaze to control the applied optical power. However, only limited series of optical power values might be applied to the lenses. These non-continuous values of optical power might result in an uncomfortable experience for the subject.

In document US20120194781A1 a system using dynamic focus Alvarez lenses and the corneal reflections is proposed to correct presbyopia.

In addition, pupil tracking is a widely used technique in many fields, from marketing to medicine, and also videogames. Being such a popular technique there are many alternatives to implement it.

For example, an highly parallelized implementation to perform pupil tracking at high-speed and with great precision by means of using graphic processors (GPUs) has been proposed by Mompeán, J., Aragón, J. L., Prieto, P., & Artal, P. ("GPU-Accelerated High-Speed Eye Pupil Tracking System". In 27th International Symposium on Computer Architecture and High Performance Computing, SBAC-PAD, pp. 17-24, October 2015).

Another method to understand the relation between the dynamics of the pupil and the accommodation of the eye has been proposed by Emmanuel Chirre, Pedro Prieto & Pablo Artal ("Dynamics of the near response under natural viewing conditions with an open-view sensor", In Biomed. Opt. Express 6, 4200-4211, 2015). This information is used in the training and the control of the subject's responses.

SUMMARY OF THE INVENTION

The object of the invention presented in this patent is to provide a method and an instrument for the automatic binocular presbyopia correction in real-time without any action from the subject.

The invention provides an optoelectronic binocular instrument for the presbyopia correction, comprising:
- a high-speed pupil tracking system, which comprises:
  - an image capturing subsystem of the eyes of the subject being corrected for presbyopia, comprising at least a camera and several light sources directed towards the eyes, and
  - an image processing subsystem to calculate the pupil size and the interpupillary distance, able to process the images of both eyes using a high-performance implementation based on the use of a graphic processor (GPU) and a highly parallel algorithm for pupil tracking, and
- two optoelectronic lenses which provide a variable optical power, and which are able to be in front of the subject's eyes being corrected for presbyopia, one in front of each eye.

Cameras are used to perform pupil tracking, and the lenses are in charge of applying the desired optical correction at each moment.

The invention also provides a method for the binocular correction of the presbyopia, which uses an optoelectronic binocular instrument for the binocular correction of the presbyopia from the previous claims, and comprising a first phase of calibration and a second phase of presbyopia correction with the following stages:

a) Calibration phase:
- The subject being corrected for presbyopia looks at a far target placed at a distance $d_{far}$,
- Images are captured using the capturing images subsystem,
- The captured images are processed by the image processing subsystem and the pupil size $S_{far}$ and the interpupillary distance are calculated, The subject being corrected looks at a near target placed at a distance $d_{near}$, Images are captured by the capturing images subsystem, The captured images are processed by the image processing subsystem and the pupil Size $S_{near}$ and the interpupillary distance are calculated, b) Presbyopia correction phase.

Images are captured by the capturing images subsystem,

The captured images are processed by the image processing subsystem and the pupil Size $S_{current}$ and the interpupillary distance are calculated, The distance D where the subject is looking is calculated using these formulas:

$$D=d_{near}+[(d_{far}-d_{near})/(s_{far}-s_{near})]*(s_{current}-s_{near})$$

$$D=(H/2)*\tan(90-\alpha), \text{ where } \alpha=a\tan(d/r),$$

wherein d is the distance that the pupils have moved, α is the angle that the eyes have turned, r is the radius of the eye, and H is the interpupillary distance of the subject while looking at infinite, The optical power to be applied in the optoelectronic lenses is calculated from the distance D, and The calculated optical power is applied to the optoelectronic lenses, wherein the stages of the presbyopia correction phase are performed continuously several times.

The correction is guided through the information received from an own system of tracking the properties of size, shape and position of the pupils of the eye.

This invention performs a continuous tracking of the size and position of each eye's pupil. Those parameters are used to calculate the correction that must be applied in each moment to the lenses or optoelectronic systems or variable focus optomechanics. The pupil tracking is performed by means of capturing an image of both eyes with a camera and providing proper Illumination. Then processing the image using a high-performance and parallel implementation of an algorithm for pupil detection in a graphic processor (GPU).

DETAILED DESCRIPTION OF THE INVENTION

The present invention consists of a method which enables automatic and binocular correction of the eye's presbyopia in real time, and the instrument associated. Furthermore, the method has three different ways of controlling the applied correction.

Figure 1:
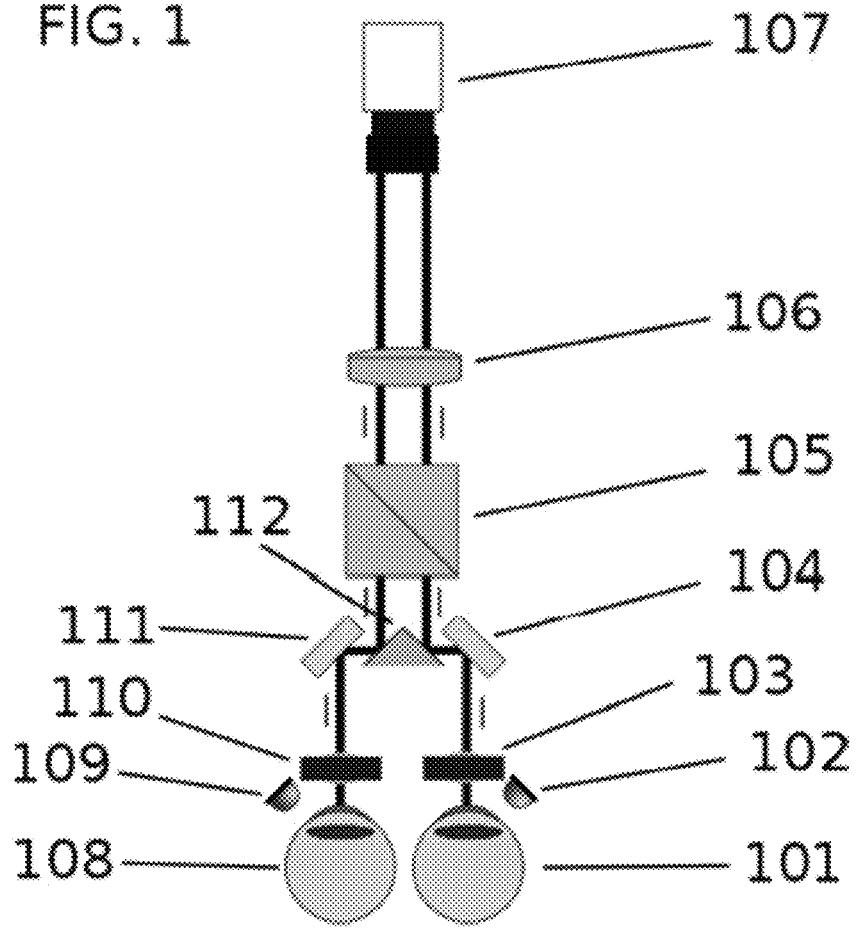
FIG. 1 shows a graph of a binocular optoelectronic instrument for presbyopia correction according to this invention.
Figure 2:
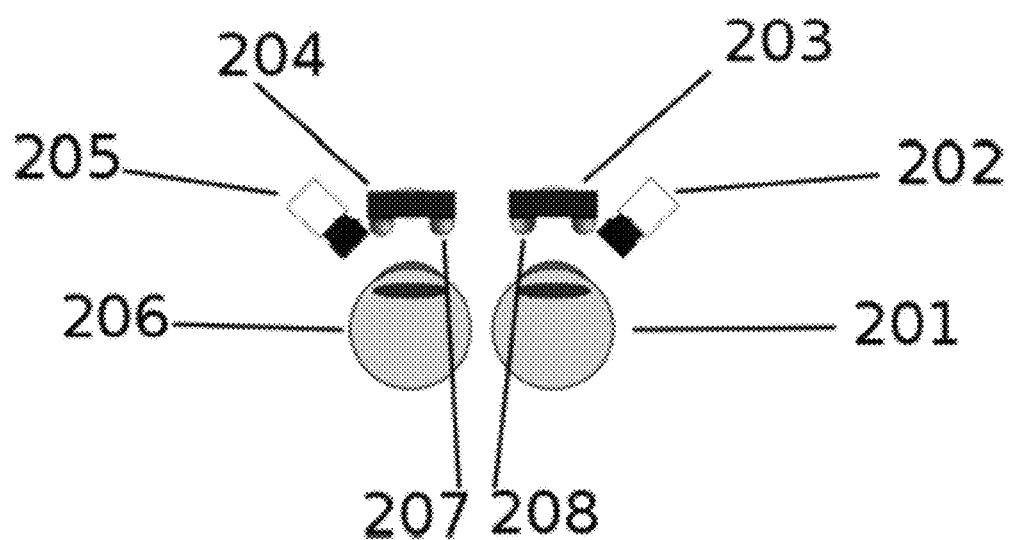
FIG. 2 shows a graph of a simplified version of a binocular optoelectronic instrument for presbyopia correction according to this invention.

The most important parts for the practical implementation of the instrument, which enables the method presented in this invention, are shown in the schemes in FIGS. 1 and 2. FIG. 2 is a simplified version of the instrument. The system in FIG. 1 includes two LEDs for infrared illumination 102, 109; the illumination is necessary so the camera 107 can capture good quality images. In addition, the system has two optoelectronic lenses 103, 110, which are placed in front of the subjects eyes 101, 108. They are used to apply the calculated optical power so the subject can focus the targets. On the other hand, the system has several mirrors 104, 105, 111, 112 and a lens 106 to focus correctly the image of the pupils in the camera. The system takes images continuously, which are processed by the pupil tracking subsystem. A high-performance parallel implementation is used to do the pupil tracking using a graphic processor (GPU). With the obtained parameters about the size and position of both pupils the optical power that the lenses 103, 110 must apply to correct the presbyopia of the subject is calculated. Finally, the correction is applied to the subject with the optoelectronic lenses 103, 110.

FIG. 2 shows a scheme of a simplified version of the optical instrument presented in this invention. The system has two infrared LED for Illuminating 207, 208; the illumination is necessary for the cameras 202, 205, so they can capture good quality images. Furthermore, two optoelectronic lenses 203, 204 are placed in front of the eyes of the subject 201, 206. Like in the not simplified version, the system captures images continuously, which are then processed by the pupil tracking subsystem. Then, the obtained information is used to calculate the optical power that the lenses 203, 204 have to apply to correct the subject's presbyopia. Finally, the correction is applied using the optoelectronic lenses 203, 204.

Figure 3:
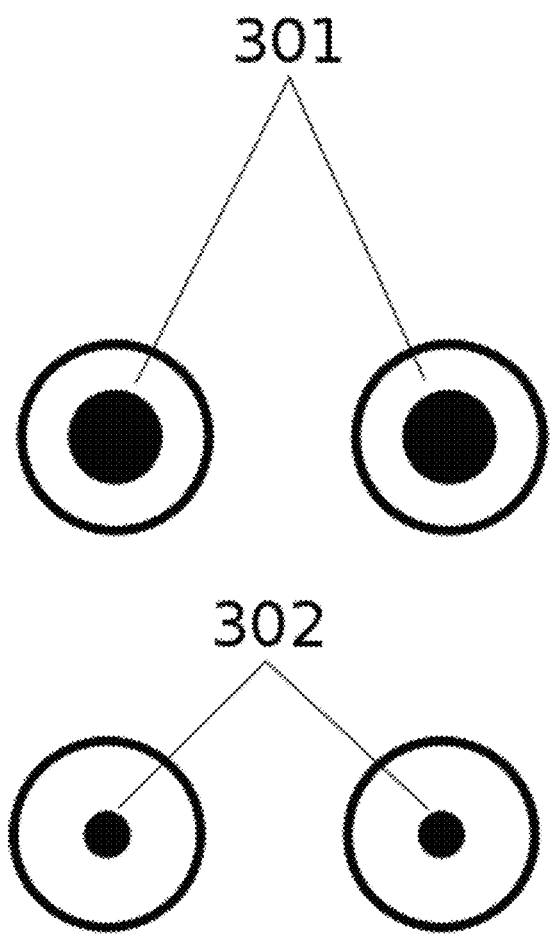
FIG. 3 shows the change in the pupil size generated when the human eye looks to a far target and a near target.

The pupil of the human eye decreases and increases its size when it focuses stimuli depending on the distance where they are at. FIG. 3 shows a scheme of the contraction of the eye's pupil while looking at near targets 302, and the dilation of the eye's pupil while looking at far targets 301. This effect is used in the described method to calculate the distance where the subject is looking at and, therefore, to determine the optical power that should be applied to the lenses, being one of the three methods presented here to calculate that value. When the calibration is performed the size of the pupil is calculated and stored while the subject is looking at both a far and a near target. This information is later used in the correction phase to interpolate the distance at which the subject is looking at. This is the used formula:

$$D=d_{near}+[(d_{far}-d_{near})/(s_{far}-s_{near})]*(s_{current}-s_{near})$$

Figure 4:
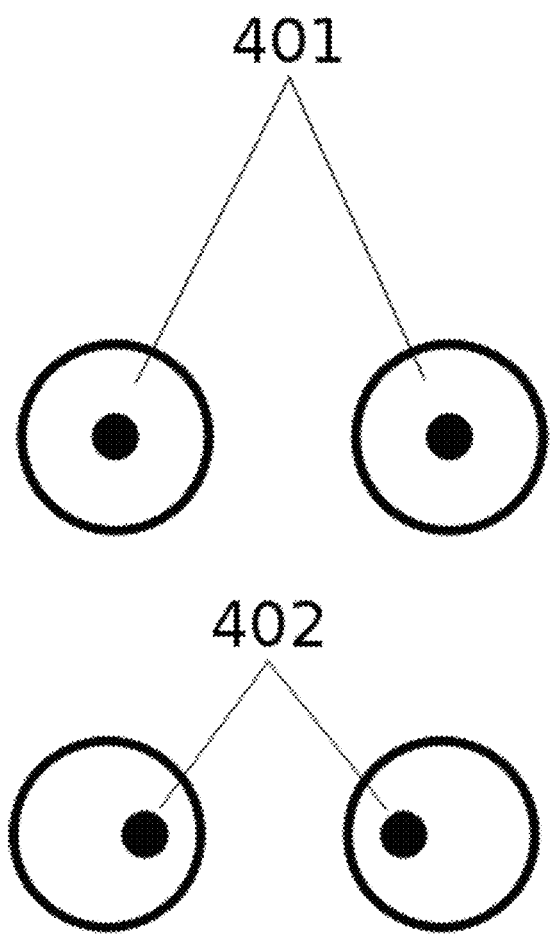
FIG. 4 shows the change in the position of the pupil generated when the human eye looks at both a far target and a near target.

Moreover, the human eye also converges and diverges while focusing targets depending on the distance where they are placed. FIG. 4 shows a scheme of the convergence of the eye while looking near targets 402 and the divergence of the eye pupil while looking at far targets 401. This behaviour is used in the described method to calculate the distance where the subject is looking at. This information is used to calculate the optical power that should be applied to the lenses, being the second of the three methods presented here to calculate that value. To calculate the distance where the subject is looking, using the interpupillary distance, this formula is used:

$$D=(H/2)*\tan(90-\alpha), \text{ where } \alpha=a\tan(d/r),$$

In that formula d is the distance that the pupils have moved, α is the angle that the eyes have turned, r is the radius of the eye and H is the interpupillary distance of the subject while looking at Infinite.

First, the angle α of the rotation of the eyes while looking at a near target is calculated. To do it the distance d with movement of the pupils is used and radius r of the eye. After calculating the angle α that the eye has rotated, the distance D, where the subject is looking, can be calculated using the previous formula, although previously the interpupillary distance H of the subject must have been measured while looking at far.

A third, more accurate, way of calculating the distance where the subject is looking at consists of combining both, the size of the pupils and the vergence of the pupils. Additionally, it is possible to obtain information about the temporal dynamics of the pupil which are related to the distance of the object to obtain information about the required optical power to be applied. This is a "learning" method.

Figure 5:
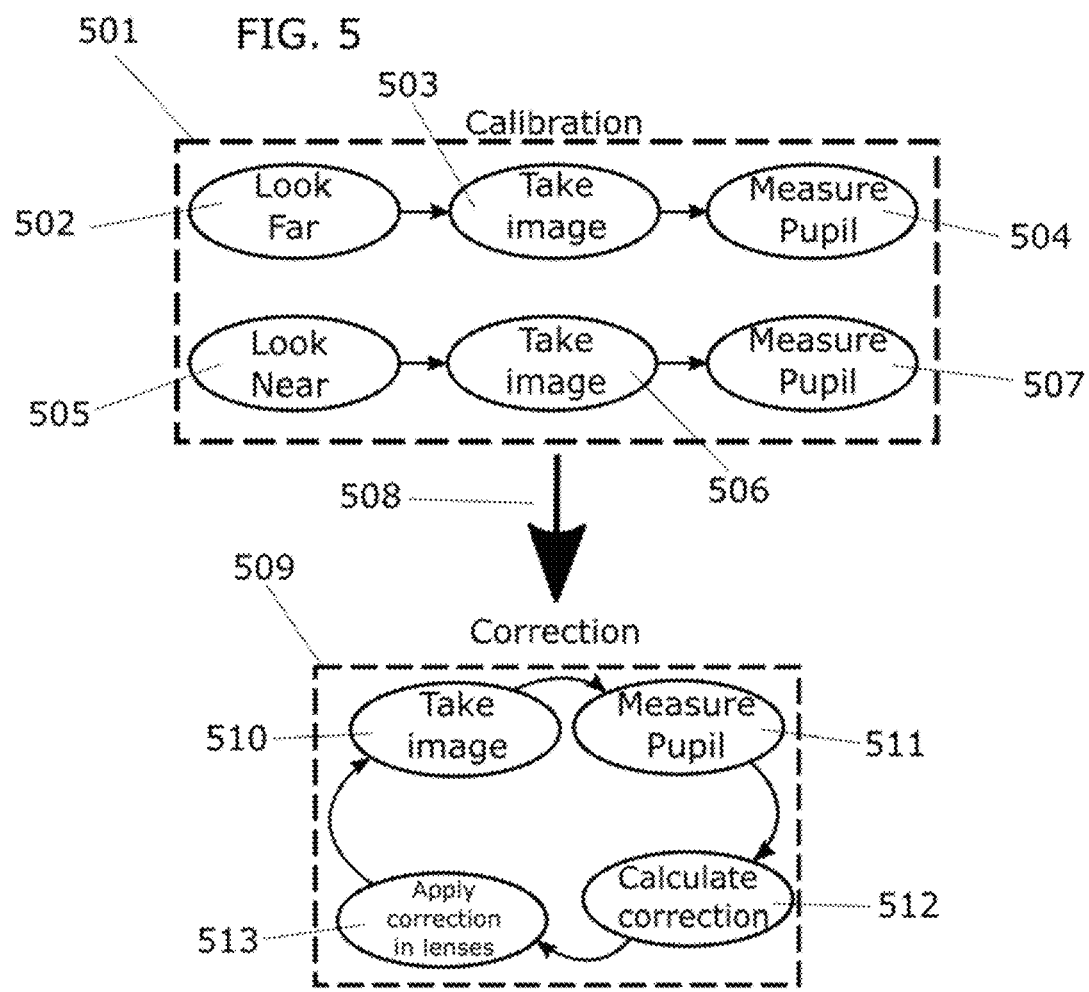
FIG. 5 shows a graph of the method for binocular correction of the presbyopia in real-time, which includes a calibration phase and a correction phase with their corresponding stages.

The described method in the present invention is shown in a scheme in FIG. 5. First, a calibration of the subject is done 501. The subject is asked to look at far 502 and a series of images are captured 503. Finally those images are processed with the image processing subsystem to calculate the size of the pupils and the interpupillary distance 504. Later the subject is asked to look at a near target 505 and another series of images are captured 506. Those images are processed with the image processing subsystem to calculate the size of the pupils and the Interpupillary distance. The information of the calibration phase can be used in the learning stages to perform an automatic optimization. Then the method moves on 508 to the correction phase 509. The correction phase 509 works continuously, starting always with the capture of an image of the subject's pupils 510. Then the image processing subsystem processes that image to obtain the size of the pupils and the interpupillary distance 511. Afterwards, the correction is calculated 512 using one of the three methods described previously. Finally, the new calculated optical power is applied to the optoelectronic lenses 513 to allow the subject to correctly focus the object.

Figure 6:
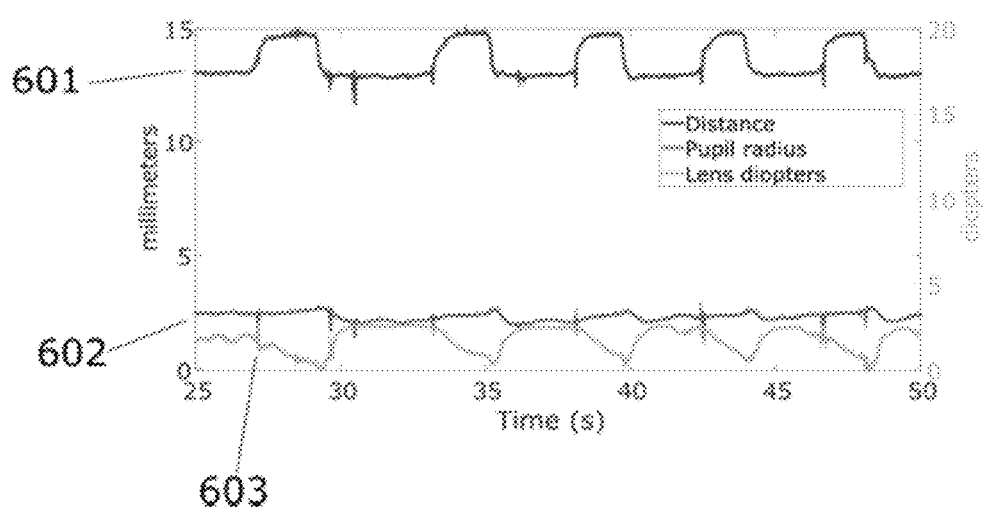
FIG. 6 shows a plot where the operation of the instrument of the invention is shown.
Figure 7:
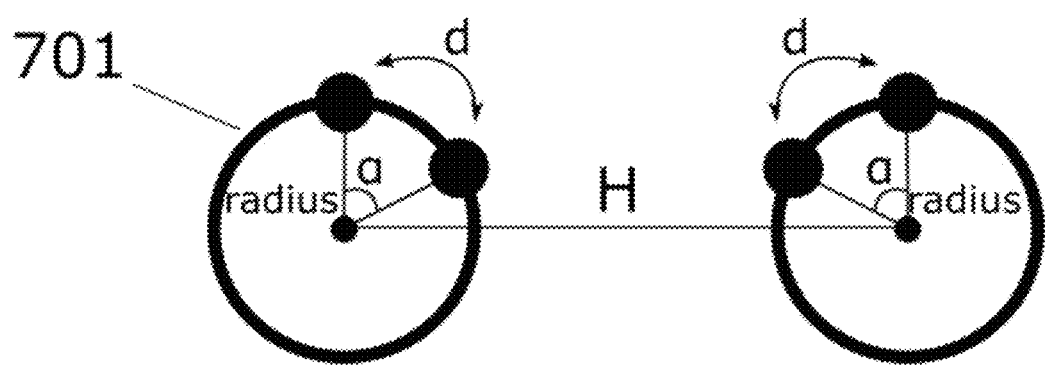
FIG. 7 shows a scheme of the angle of the eyes while looking at a near target.

FIG. 6 includes an example where the operation of the system is shown. In the plot, the X axis shows the time, the left Y axis shows the scale of the size and distance between the pupils in millimetres, and the right Y axis shows the scale of the diopters applied by the lens. The first line of the plot 601 shows the distance between both pupils along time; the second line 602 shows the radius of the pupil; while the third line 603 shows the diopters applied to the optoelectronic lenses. As expected, increasing the interpupillary distance increases also their size and decrease the amount of diopters applied to the lenses. Also, decreasing the interpupillary distance, decreases their size and it increases the amount of diopters applied to the optoelectronic lenses.

The implementation of the pupil tracking system uses a highly parallelized algorithm for graphic processors (GPUs) achieving a very high-speed, therefore, enabling the processing of a big number of samples per second. This processing speed reduces the latency of the system and increases its robustness and accuracy allowing the system to react very fast to changes in the subject's pupil, also reducing the total system latency and improving the user experience. The pupil tracking algorithm searches the border of the pupil of the eye. First, it performs a preprocessing of the captured image to remove the reflections generated by the infrared Illumination and reduce the noise that might be in the image. Then, starting from an initial position, the pixels around it are tested searching for a big change in the gradient, since the border of the pupil usually has a big change in the gradient. Finally, the found border points are randomly selected and several ellipse fittings are performed. To choose the best fitting ellipse the distance between all the ellipses and all the points is calculated and the one with the smallest distance is selected.

The next numerical references are linked to different elements which are part of the invention and steps described, as represented in the present document.

101. Right subject's eye.
102. Infrared LED illumination.
103. Optoelectronic lens.
104. Flat mirror.
105. Dichroic mirror.
106. Lens.
107. Camera for pupil tracking.
108. Left subject's eye.
109. Infrared LED illumination.
110. Optoelectronic lens.
111. Flat mirror.
112. Prism mirror.
201. Right subject's eye.
202. Camera for pupil tracking.
203. Optoelectronic lens.
204. Optoelectronic lens.
205. Camera for pupil tracking.
206. Left subject's eye.
207. Infrared LED illumination.
208. Infrared LED illumination.
301. Subject's pupils looking a far target.
302. Subject's pupils looking a near target.
401. Subject's pupils looking a far target.
402. Subject's pupils looking a near target.
501. Calibration process.
502. Far looking state.
503. Taking picture state.
504. Measuring the pupil state.
505. Near looking state.
506. Taking picture state.
507. Measuring the pupil state.
508. Transition from calibration to processing.
509. Correction process.
510. Taking picture state.
511. Measuring the pupil state.
512. Calculating the correction state.
513. Applying correction to the lenses state.
601. Line showing the interpupillary distance.
602. Line showing the pupil's radius.
603. Line showing the diopters applied to the lens.
701. Scheme of the movement of a human eye while converging the gaze.

The invention claimed is:

1. Optoelectronic binocular instrument for the presbyopia correction, characterized in that it comprises:

A high-speed pupil tracking system, which comprises:
An image capturing binocular subsystem of the eyes of the subject being corrected for presbyopia, comprising at least a camera (107; 202, 205) and several light sources (102, 109; 207, 208) directed towards the eyes, and
An image processing binocular subsystem to calculate the pupil size in each eye and the interpupillary distance, able to process the images of both eyes using a high-performance implementation based on the use of a graphic processor (GPU) and a highly parallel algorithm for pupil tracking, and Two optoelectronic lenses (103, 110; 203, 204) which provide a variable optical power, and which are able to be in front of the subject's eyes being corrected for presbyopia, one in front of each eye.

2. Optoelectronic binocular instrument for the presbyopia correction, according to claim 1, where the light sources (102, 109; 207, 208) are infrared illumination LEDs.

3. Optoelectronic binocular instrument for the presbyopia correction, according to claim 1, that additionally comprises several mirrors (104, 105, 111, 112), and at least one lens (106) to focus the image of the subject's eyes pupils being corrected for presbyopia in at least one camera (107; 202, 205).

4. Optoelectronic binocular instrument for the presbyopia correction, according to claim 3, where the mirrors are flat mirrors (104, 111), dichroic mirrors (105), and prism mirrors (112).

5. Method for the binocular correction of the presbyopia, which uses an optoelectronic binocular instrument for the binocular correction of the presbyopia from claim 1, and comprising a first phase of calibration and a second phase of presbyopia correction with the following stages:

a) Calibration phase:
- The subject being corrected for presbyopia looks at a far target placed at a distance $d_{far}$,
- Images are captured using the capturing images subsystem,
- The captured images are processed by the image processing subsystem and the pupil size $S_{far}$ and the interpupillary distance are calculated,
- The subject being corrected looks at a near target placed at a distance $d_{near}$,
- Images are captured by the capturing images subsystem,
- The captured images are processed by the image processing subsystem and the pupil Size $S_{far}$ and the interpupillary distance are calculated, b) Presbyopia correction phase,
- Images are captured by the capturing images subsystem,
- The captured images are processed by the image processing subsystem and the pupil Size $S_{far}$ and the interpupillary distance are calculated,
- The distance D where the subject is looking is calculated using these formulas:

$$D=d_{near}+[(d_{far}-d_{near})/(s_{far}-s_{near})]*(s_{current}-s_{near})$$

$$D=(H/2)*\tan(90-\alpha), \text{ where } \alpha=a\tan(d/r),$$

wherein d is the distance that the pupils have moved, $\alpha$ is the angle that the eyes have turned, r is the radius of the eye, and H is the interpupillary distance of the subject while looking at infinite,

- The optical power to be applied in the optoelectronic lenses (103, 110; 203, 204) is calculated from the distance D, and
- The calculated optical power is applied to the optoelectronic lenses (103, 110; 203, 204), wherein the stages of the presbyopia correction phase are performed continuously several times.

6. Method for the binocular correction of the presbyopia, according to claim 5, wherein the highly parallelized algorithm for pupil tracking performs the next sequence of actions:
- Preprocessing of the captured image to remove reflections produced by the illumination and removing noise that might be in the image;
- Next, a starting position is used to explore pixels around it, searching for big changes in the gradient, which might be indicative of the border of the pupil;
- Some points are randomly selected from those that have been found and several adjustments are made to an ellipse; and
- To choose the ellipse that best fits the pupil, the distance between the ellipses and the points previously found is calculated, and the one with the smallest distance is selected.

* * * * *